US012313738B2

(12) United States Patent
Goldberg et al.

(10) Patent No.: US 12,313,738 B2
(45) Date of Patent: May 27, 2025

(54) MOTION TRACKING USING PURE TONES

(71) Applicant: REVIVA SOFTWORKS LTD, London (GB)

(72) Inventors: Jules Goldberg, London (GB); Filippos Ineglis, London (GB)

(73) Assignee: REVIVA SOFTWORKS LTD, London (GB)

( * ) Notice: Subject to any disclaimer, the term of this patent is extended or adjusted under 35 U.S.C. 154(b) by 89 days.

(21) Appl. No.: 18/548,468

(22) PCT Filed: Feb. 2, 2022

(86) PCT No.: PCT/GB2022/050276
§ 371 (c)(1),
(2) Date: Aug. 30, 2023

(87) PCT Pub. No.: WO2022/185025
PCT Pub. Date: Sep. 9, 2022

(65) Prior Publication Data
US 2024/0183979 A1 Jun. 6, 2024

(30) Foreign Application Priority Data

Mar. 1, 2021 (GR) .............................. 20210100120
Mar. 23, 2021 (GB) ..................................... 2104031
(Continued)

(51) Int. Cl.
*G01S 15/62* (2006.01)
*A61B 5/00* (2006.01)
*A61B 5/11* (2006.01)
(52) U.S. Cl.
CPC ............ *G01S 15/62* (2013.01); *A61B 5/1126* (2013.01); *A61B 5/7257* (2013.01)

(58) Field of Classification Search
CPC ... G08B 13/196; G08B 13/19634; G06F 1/16; G06F 1/163; G01N 29/00; G01N 29/046;
(Continued)

(56) References Cited

U.S. PATENT DOCUMENTS 6,874,364 B1 * 4/2005 Campbell ............ G01N 29/046
73/659
10,226,234 B2 * 3/2019 Specht ................. A61B 8/4488
(Continued)

FOREIGN PATENT DOCUMENTS

| EP | 3414598 A2 | 12/2018 |
| GB | 2437619 A | 10/2007 |
| WO | 2018050913 A1 | 3/2018 |

OTHER PUBLICATIONS

International Preliminary Report on Patentability re PCT/GB2022/050276 dated May 25, 2023 (31 pages).
(Continued)

*Primary Examiner* — Van T Trieu
(74) *Attorney, Agent, or Firm* — Aurora Consulting LLC; Kristen J. Hansen

(57) ABSTRACT

Apparatus is provided to detect motion of a target reflecting one or more pure tone signals, comprising transmission of one or more pure tone acoustic signals, reception of the signal reflected by a target ensonified by the transmitted signal, and motion detection of the ensonified target from analysis of the Discrete Fourier Transform (DFT) of the received signal, in particular values of the time-variance of energy within adjacent frequency bins in the signal DFT, where the emitted tone has a frequency at the boundary between the two adjacent frequency bins.

20 Claims, 9 Drawing Sheets

(30) Foreign Application Priority Data

Jun. 16, 2021 (GR) .............................. 20210100397
Jun. 23, 2021 (GB) .................................... 2109002
Dec. 21, 2021 (GB) .................................... 2118676

(58) Field of Classification Search
CPC ..... G01N 29/0609; G01S 15/58; G01S 15/62;
G01S 15/66; G01S 7/534; A61B 5/00;
A61B 5/11; A61B 8/00; A61B 8/08;
H04N 7/18
See application file for complete search history.

(56) References Cited

U.S. PATENT DOCUMENTS

| | | | |
|---|---|---|---|
| 12,190,627 B2* | 1/2025 | Call | .................. G06V 40/1306 |
| 2008/0231705 A1* | 9/2008 | Keller | .............. G08B 13/19634 |
| | | | 348/154 |

OTHER PUBLICATIONS

International Search Report re PCT/GB2022/050276 dated Aug. 4, 2022 (3 pages).
Written Opinion re PCT/GB2022/050276 dated Oct. 13, 2022 (9 pages).

* cited by examiner

MOTION TRACKING USING PURE TONES

CROSS-REFERENCE TO RELATED APPLICATIONS

This application is a 35 U.S.C. 371 National Stage filing for PCT Application Ser. No. PCT/GB2022/050276, filed Feb. 2, 2022, now published as WO 2022/185025, which claims priority to GB Application No. 2118676.2, filed on Dec. 21, 2021, which claims priority to GB Application 2109002.2, filed on Jun. 23, 2021, which claims priority to GR Application No. 2021-02290, filed on Jun. 16, 2021, which claims priority to GB Application No. 2104031.6, filed on Mar. 23, 2021, which claims priority to GR Application No. 2021-00824, filed on Mar. 1, 2021, the contents of each of which are herein incorporated by reference in their entireties.

FIELD OF INVENTION

The present invention relates to a method and apparatus for tracking motion of a target, and particularly, but not exclusively, down to less than 10 cm/s, using pure tones.

TECHNICAL BACKGROUND

Motion sensors are components used in a wide variety of systems, for example, to enable interactions with devices such as smartphones, for gaming, security, and for medical applications including sleep tracking.

The most commonly used motion sensors are three-axis accelerometers integrated into smart devices to detect physical movements. These require direct contact between the device and the user to detect the user's motion, for example, when a smartphone is picked up a motion sensor detects activity which can trigger the smartphone to light up the screen; or sleep tracking based on movements of a wrist-worn actigraphy device. Such devices can restrict the user's motion, for example, requiring them to physically interact with a smartphone to light up the screen, or be uncomfortable, for example wearing a wrist-worn device in bed for sleep tracking.

Contactless motion detection has thus emerged as an alternative, generally based on transmission and reflection of electromagnetic or ultrasonic waves. For example, contactless sleep tracking has been demonstrated using radio waves, whilst motion sensors in home-security systems typically detect heat energy released by humans. Most techniques require specialised transmitters and receivers making them inaccessible to most users.

There are prior examples of sound-based, contactless motion detection using hardware readily available in smartphones. However, these approaches have been limited in accuracy and sensitivity and can be uncomfortable to use.

One existing method of sound-based, contactless motion detection uses reflections of a frequency-modulated sound signal, or "chirp". The advantages of chirps are well-known in a number of large-scale devices such as imaging radar, but in applications for personal use, for example sleep tracking in a domestic environment, a chirp sound signal can be particularly apparent to the human ear on account of the ear's sensitivity to changes in frequency, even in a low-ultrasonic range (between 16 kHz-20 kHz).

Motion detection methods using pure tones have previously been demonstrated, but these use much higher energy levels and do not show the same accuracy achievable with the embodiments of the present invention.

SUMMARY OF INVENTION

Embodiments of the present invention aim to address the limitations associated with conventional motion detection techniques.

Embodiments of the present invention provide methods to track motion of a target reflecting one or more pure tone signals, containing the following steps:
1. transmission of one or more pure tone acoustic signals;
2. reception of the signal reflected by a target ensonified by the transmitted signal;
3. motion estimation of the ensonified target from analysis of the Discrete Fourier Transform (DFT) of the received signal, in particular time-variance of energy values within at least adjacent frequency bins, where the emitted tone is a "boundary tone" with a frequency at the boundary between the two adjacent frequency bins.

As a result of the steps above, it becomes possible to estimate motion of a target slower than 10 cm/s, and its direction relative to a microphone receiving the signal reflected by the target, through transmission of inaudible pure tones, achievable with hardware available on most smartphones.

According to an aspect of the present invention, there is provided an apparatus for tracking motion of a target, comprising: a speaker configured to transmit a pure tone acoustic signal; a microphone configured to sample a signal reflected by a target ensonified by the transmitted pure tone acoustic signal; and processing means configured to: control the speaker and the microphone; estimate motion of the target based on analysis of Discrete Fourier Transformation of the sampled signal, wherein the analysis is based on the time-variance of energy values in at least adjacent frequency bins around the frequency of the transmitted pure tone acoustic signal; wherein the frequency of the transmitted pure tone acoustic signal is at the boundary of the adjacent frequency bins of the DFTs; the apparatus further comprising output means configured to output the motion estimation result.

Tracking motion of the target may further comprise determining the direction of movement of the target based on the relative energy in the adjacent bins.

The processor may be further configured to infer velocity of motion of the target based on a calculation of the centroid of differential energy values, in the frequency domain, between sequential DFTs.

The analysis of Discrete Fourier Transformation of the sampled signal may comprise: performing a first DFT of the sampled signal, wherein the first DFT is based on a first number of samples; performing a second DFT of the sampled signal, wherein the second DFT is based on a second number of samples which is at least double the first number of samples; estimating motion of the target based on analysis of a combination of the first DFT and the second DFT; wherein the frequency of the transmitted pure tone acoustic signal is at the boundary of the adjacent frequency bins of the first DFT; and wherein the frequency of the transmitted pure tone acoustic signal is at the centre of the frequency bin of the second DFT containing the transmitted pure tone acoustic signal.

The processor may be further configured to estimate displacement of the target from the inferred velocity of motion of the target and a duration of the estimated motion.

According to another aspect of the present invention, there is provided a musical instrument apparatus having an output means is configured to output a sound according to one or more gestures determined from the estimated motion of the target.

According to another aspect of the present invention there is provided a gaming apparatus wherein the processing means is configured to control a game character according to one or more gestures determined from the estimated motion of the target.

The processing means may be arranged to control a user interface in accordance with one or more gestures determined from the estimated motion.

The one or more gestures may be determined from the estimated motion in only one predetermined direction.

According to another aspect of the present invention there is provided a sleep-tracking apparatus, comprising means for performing sleep analysis based on the estimated motion of the target.

The output means may be configured to output an alarm within a predetermined time of the means for performing sleep analysis determining arousal or light sleep of the target.

The output means may be configured to output an alarm or notification according to the estimated occurrence of motion.

The motion estimation result output by the output means may further comprise displaying a visual representation of estimation motion.

The processor may be further configured to determine environmental noise, and to determine a frequency of the pure tone acoustic signal from a plurality of boundary frequencies corresponding to respective boundaries between adjacent bins of the DFT, based on the environmental noise determined at each of the plurality of frequencies.

The processor may be further configured to adjust the volume of the pure tone acoustic signal in dependence upon a measurement of the energy in the received signal.

The speaker may be configured to transmit a plurality of acoustic signals, at least one of which is at the boundary of a respective pair of adjacent frequency bins in the DFT.

According to another aspect of the present invention there is provided a method for tracking motion of a target, the method comprising: transmitting a pure tone acoustic signal; sampling a signal reflected by a target ensonified by the transmitted pure tone acoustic signal; and estimating motion of the target based on analysis of Discrete Fourier Transformation of the sampled signal, wherein the analysis is based on the time-variance of energy values in at least adjacent frequency bins around the frequency of the transmitted pure tone acoustic signal; wherein the frequency of the transmitted pure tone acoustic signal is at the boundary of the adjacent frequency bins of the DFTs; wherein the method further comprises outputting a motion estimation result.

According to another aspect of the present invention there is provided a computer program which, when executed by a processor, is arranged to cause the above method to be performed.

Further advantages will become apparent from the following description.

BRIEF DESCRIPTION OF DRAWINGS

Embodiments of the present invention will now be described by way of example only, with reference to the accompanying drawings, in which:

FIG. 6b shows a composite window obtained by adding the weighted windows of FIG. 6a.

DETAILED DESCRIPTION

General Principle

Figure 1:
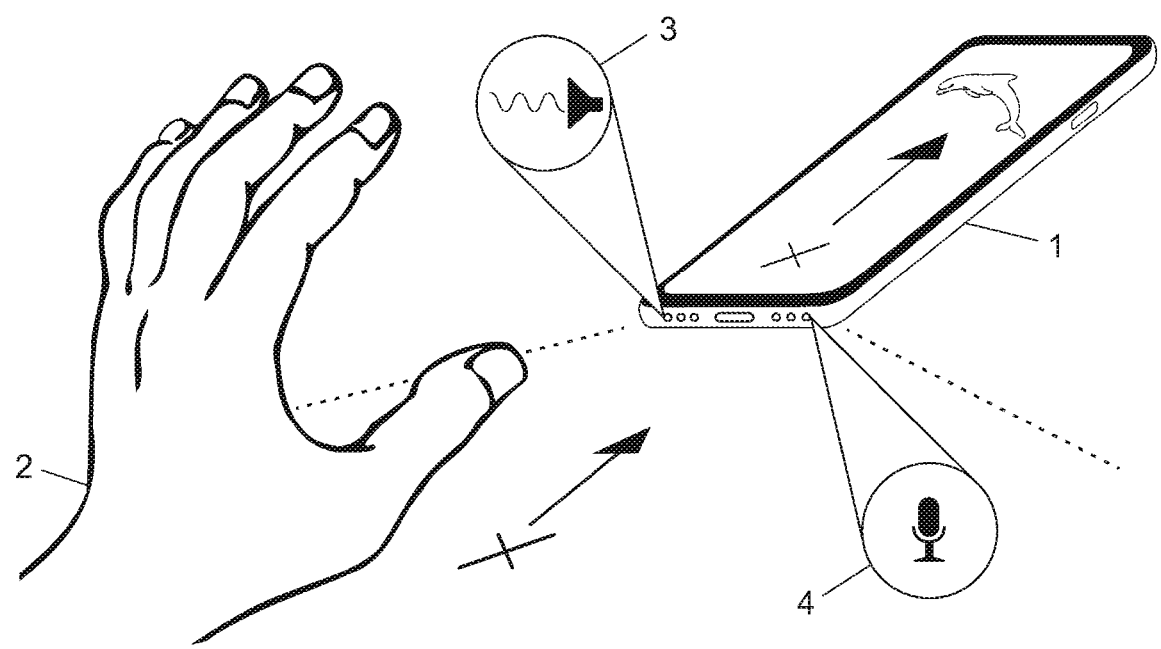
FIG. 1 shows an example of a device which may be used for tracking motion of a target according to an embodiment of the present invention.

FIG. 1 illustrates a device 1 which may be used for tracking motion of a target 2, comprising a speaker 3 and a microphone 4, according to an embodiment of the present invention. In the present embodiment, the device is a smartphone, and the target 2 is a user's hand making gestures to control the smartphone. The device comprises processing means (not shown) configured to control the speaker 3 and the microphone 4, and to execute computer-readable instructions to perform the method set out in the flow chart in FIG. 3, described in detail below, in order to track motion of the target 2.

In embodiments of the present invention, motion is tracked based on analysis of reflection of a sound wave from the target. A sound wave at a particular frequency, referred to herein as a pilot tone, is transmitted towards the target from a speaker. A substantial portion of the transmitted signal is directed straight to a microphone substantially co-located with the speaker. Reflections of the transmitted signal are reflected indirectly back to the microphone, or are reflected in a direction such that they do not reach the microphone. Part of the transmitted energy may be absorbed by the target or the environment.

If the target is moving, the frequency of the signal reflected directly back to the microphone is Doppler-shifted, as known in the art. If the target moves towards the microphone, the frequency of the reflected signal increases. If the target moves away from the microphone, the frequency of the reflected signal decreases. Generally, the change in frequency, $\Delta f$, relates to the velocity $\Delta v$ of the target in the direction towards a microphone according to $\Delta f = f_0 \cdot \Delta v / c$, where $f_0$ is the frequency of the transmitted sound signal, and c is the speed of sound in air.

As such, motion of the target can be estimated based on determination of the frequency shift of the received signal. As set out above, the signal which is received by the microphone may take a number of different paths. In cases where the target itself is relatively large, (in contrast to being represented as a point source of sound waves), it may have constituent parts moving at a range of different velocities relative to the microphone. As such, the reflected signal may exhibit a range of different frequencies. Additionally, a portion of the originally transmitted signal will reach the microphone without being reflected by the target at all (for example, via direct transmission from the speaker to the microphone, or via reflection from one or more stationary surfaces between the speaker and the microphone). This portion is, in many cases, significant, and techniques of eliminating the influence of this portion from assessment of the reflection portion, so as to improve motion estimation, are described below.

In order to determine the frequency spectrum of the signal received at the microphone, a DFT is applied to a time-series obtained by digitally sampling the received sound signal. A representation of the energy of the signal over a range of frequency bins is derived from modulus of the complex information in the DFT. Target motion is estimated through processing of these energy values.

Principle of Slow Motion Estimation

The inventors have recognised that when a target is moving what is referred to herein as "slowly", of the order of 10 cm/s or less, the information representing the Doppler shift of the moving target can be represented by a frequency shift whose size falls within the speed range spanned by a single frequency bin from the tone frequency, for a particular choice of sampling frequency and tone frequency. If sampling frequencies common in the audio industry, such as 48 kHz or 44.1 kHz, are used at the microphone, with a sample frame typically containing 2048 samples, the spacing between consecutive frequency bins of the DFT is of the order of 20-25 Hz. Where the pilot tone is approaches ultrasonic frequency (approaching 20 kHz), the Doppler shift of a target moving at 10 cm/s, using $\Delta f = f_0 \cdot \Delta v/c$, approaches 6 Hz, which is "within" a single frequency bin of the pilot tone.

In embodiments of the present invention, it is particularly advantageous to transmit a pilot tone having a single frequency, that is, a pure tone acoustic signal. Such a frequency is referred to herein as a "boundary frequency", since it occurs at the boundary between the pair of its adjacent bins.

Figure 2A:
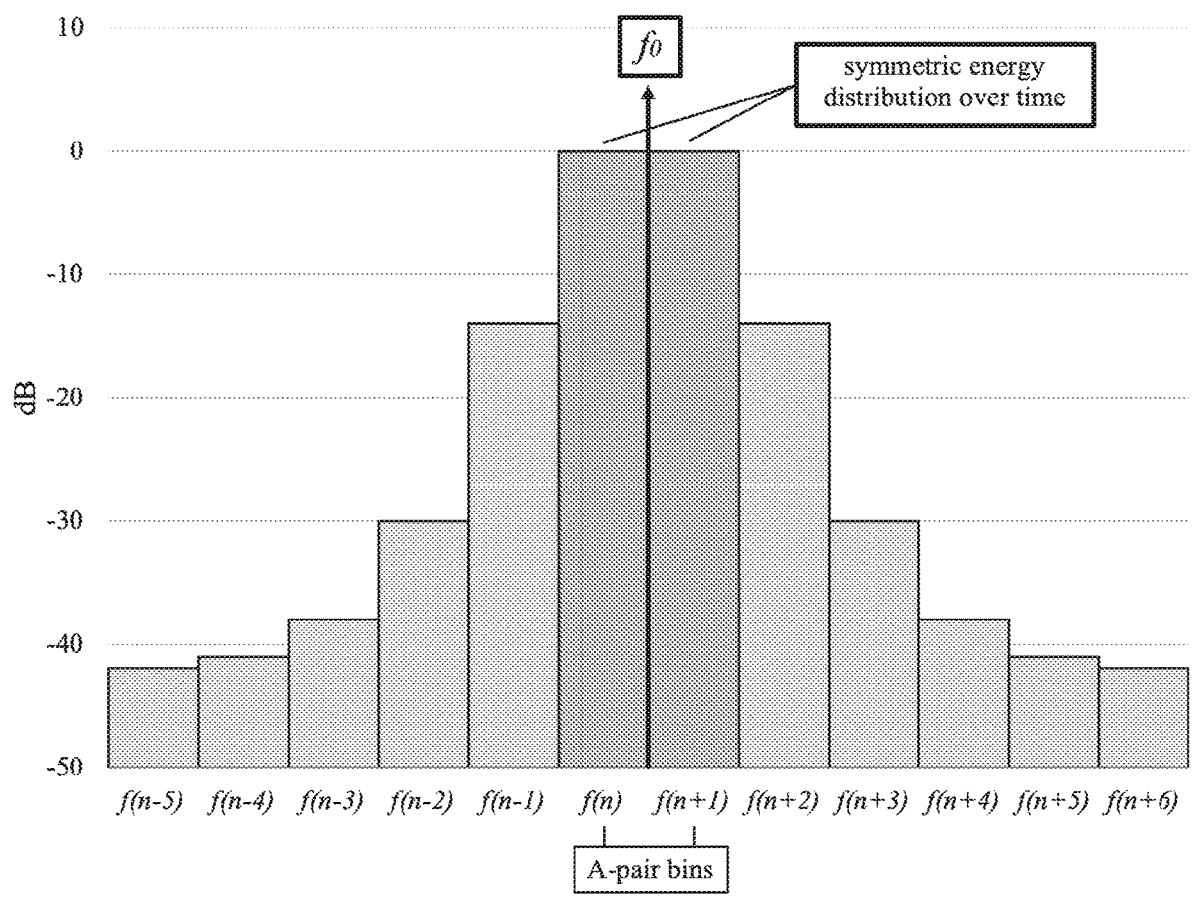
FIG. 2a illustrates the energy in the frequency domain in the case where there is no motion.
Figure 2B:
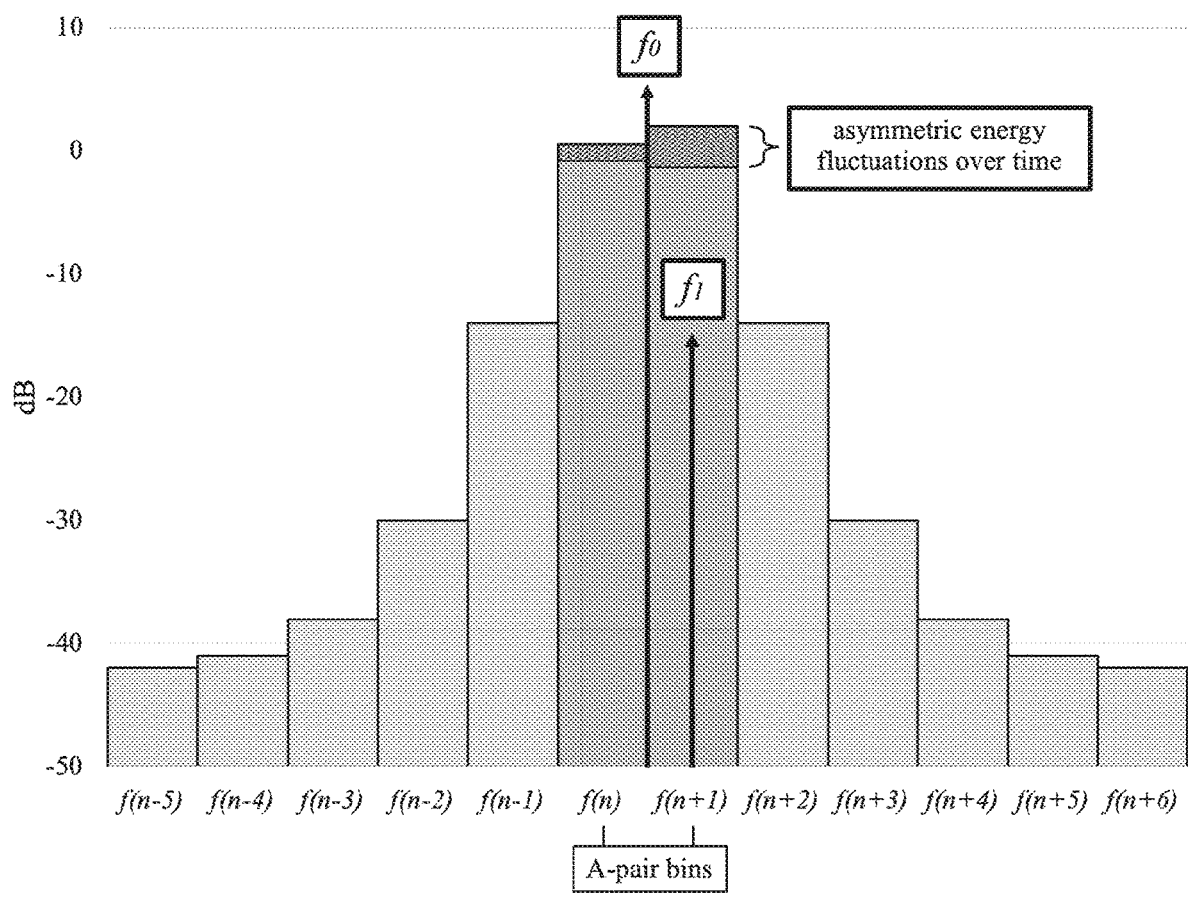
FIG. 2b illustrates the energy in the frequency domain in the case of slow motion towards the microphone.

FIGS. 2a and 2b show representations of the energy of the DFT of the sampled received signal in each of a number of different bins having centre frequencies $f_{n-5}$, $f_{n-4}$, ..., $f_n$, $f_{n+1}$, ..., $f_{n+6}$ based on transmission of a boundary tone $f_0$. FIG. 2a illustrates the energy of the DFT of the received signal in the case where there is no motion, whilst FIG. 2b illustrates the energy of the DFT of the received signal in the case where slow motion occurs, causing a reflected signal having frequency $f_1$.

Use of a boundary frequency enables accurate and sensitive estimation of motion based on a frequency shift above or below the frequency of the pilot tone, into one frequency bin or the other, by motion of the target. This appears as an asymmetric fluctuation in the energy content of the adjacent frequency bins, as shown in FIG. 2b.

In particular, when a pilot tone is at a boundary frequency, the direction of motion can be determined by the relative time-variance of the energy content represented in the adjacent pair of frequency bins $f_n$, $f_{n+1}$, centred on the boundary frequency $f_0$, also referred to herein as the "A-pair". Genuine motions can also be distinguished from external noises due to the asymmetric impact of motion on the system; an external noise will cause similar fluctuations in both A-pair bins and can therefore be eliminated. On the other hand, a motion will produce an asymmetric response. For example, fluctuation may be observed in one bin of the A-pair and relative stability may be observed in the other bin of the A-pair.

Since the majority of the information characterising slow motion is in the A-pair, velocity of a target can be inferred from knowledge of the width of the frequency bins once motion is estimated as a result of analysis of the A-pair. In some embodiments, a velocity within a range can be inferred, in which the range is associated with a Doppler shift of a frequency range corresponding to the width of the A-pair bins.

As set out above, the majority of the energy of the received signal is associated with the "direct" path from the speaker to the microphone, which is dominant in the energy content of the DFT bins adjacent to the pilot tone. Reflections of the pilot tone account for a minority of the energy which is superposed to the direct path energy. In a typical usage scenario in which a user's hand makes gestures near a smartphone, the Doppler shifted energy in one bin of the A-pair, containing a dominant pilot tone signal, is approximately 10% of the pilot tone energy.

In addition, as the Doppler shifted energy is out of phase with the direct path energy, the total energy in the A-pair may be higher or lower than it would otherwise be without the Doppler signal, with only small changes to the average energy content of the A-pair over time. Interference between the reflected signal and the transmitted pilot tone may therefore lead to the energy content of a particular frequency bin increasing (due to constructive interference) or decreasing (due to destructive interference). Frequency bins containing a strong interfering reflected signal therefore exhibit greater fluctuations in their energy content over a sequence of sample frames, compared with frequency bins which contain a weaker reflected signal. The energy content of the frequency bins may also be affected by a change in the environment of the target.

Thus, in addition to direct comparison of the energy in the adjacent pair of frequency bins, a comparison of their relative time-variance is also performed in embodiments of the present invention. This method is also referred to herein as "differencing", and involves measuring the energy fluctuations in frequency bins by observing the absolute differences between readings of the energy content of the frequency bins over time, obtained via a sequence of DFTs. For example, an increased level of activity, whether an increase or decrease, or both, of energy content of one of the two bins over a sequence of sample frames compared with the other bin would be readily indicative of motion. Such volatility is represented in FIG. 2b by a variable energy content of the A-pair bins when a series of spectra are superposed.

Since the transmitted pilot tone energy component is substantially constant between adjacent sample frames, whereas the reflected signal energy component is variable in accordance with the target motion, differencing is an effective method for eliminating redundant energy information from the motion estimation process, specifically, the transmitted pilot tone energy component common to successive DFTs.

If a frequency other than a boundary frequency were to be used to detect slow motion, energy fluctuations in the DFT would be such that it would not be possible to determine directionality of the motion.

In summary, a boundary frequency enables directional estimation of slow motion speeds, due to the resulting asymmetric response in the A-pair.

In addition, the asymmetric responses which are described above can be obtained with a pilot tone having low energy relative to environmental noise, in addition to the tone being in an inaudible frequency range. The sensitivity of the described motion estimation is such that an asymmetric response in the A-pair is highly indicative of motion of the target, and such asymmetry presents in the absence of a high-energy pilot tone. Low-energy pilot tones have associated advantages with respect to the energy consumption of the supporting hardware, and in combination with the slow motion speeds which can be estimated, leads embodiments of the present invention to be highly sensitive and highly efficient.

In the case of no motion, as shown in FIG. 2a, the energy of the DFT of the received signal is distributed symmetrically about the boundary tone. The symmetry of the bins about the boundary tone enables highly accurate estimation of zero velocity, as the energy in these bins is substantially equal. During analysis of the bin energies, described in more detail below, it is possible to apply oppositely-signed weightings to the bins on either side of the boundary tone, and in this instance, the sum of the energy distributed across the bins substantially sums to zero.

Boundary Frequency Calculation

The following equations describe how to calculate a specific boundary frequency $f_0$, given a sample rate $f_s$ and a guide tone frequency $f_g$ representing an approximation of a desired boundary frequency in embodiments of the present invention. The DFT consists of N frequency points that span the range of frequencies from 0 Hz to $f_s$ Hz.

The frequency step between consecutive frequency bins is:

$$\text{step} = f_s/N.$$

The floor function gives the index of the first bin, k, whose central frequency is below the target tone frequency $f_g$, such that:

$$k = \text{Floor}(f_g/\text{step}).$$

Assuming the boundary frequency is to be between the $k^{th}$ and the $(k+1)^{th}$ bins, it can be determined by calculating the average of the central frequencies of these two bins:

$$f_0 = \text{step}(k+(k+1))/2.$$

For example, for $f_s=48$ kHz, N=2048, and $f_g=18$ kHz, the boundary frequency is $f_0=18{,}011.72$ Hz.

Optimum performance may be achieved when $f_0$ is on the boundary frequency to the nearest 1 Hz, or, if larger frequency bins (approximately 20 Hz) are used when N=2048, substantially at the boundary frequency within a tolerance of the order of 2-3 Hz.

In embodiments of the present invention, a boundary frequency is used for the pilot tone which is inaudible to humans. In contrast to a chirp, it is generally found that human sensitivity to single frequency tones is lower than to variable frequency tones, and so frequencies as low as 16 kHz may be inaudible.

Motion Tracking Method

A target motion tracking method according to embodiments of the present invention is provided, as illustrated with reference to FIG. 3 and described in conjunction with the apparatus 100 described with reference to FIG. 4.

At step S10, a pilot tone is transmitted towards the target from a speaker 300. As described above, a pilot tone having a boundary frequency is transmitted such that motion of the target is estimated sensitively and accurately based on a frequency shift above or below the frequency of the pilot tone. In some embodiments, the pilot tone has a frequency which is substantially inaudible to humans (for example, above 16 kHz). In the example described above, the boundary frequency is calculated to be 18,011.72 Hz.

At step S20 a sound signal, including the reflection of the pilot tone by the target, is received by a microphone 200 and digitally sampled at a sampling frequency of, for example, 48 kHz. The microphone 200 is controlled by a processor 400 of the apparatus 100 which causes the microphone to record for a predetermined time period, such that a particular number of samples of the received signal is collected based on the sampling frequency, the samples arranged in a plurality of sample frames.

In some embodiments, a sample frame contains 2048 samples. In alternative embodiments, a sample frame contains 4096 samples. The number of samples in the frame affects the width of the frequency bins to be obtained in the DFT as described above, and the sample frame size thus affects the speed of motion which can be estimated. The sample frame size can be of size $2^n$, depending on a particular application of the method, and the desired sensitivity. The use of such a sample frame size enables the DFT to be readily implemented as a Fast Fourier Transform, as known in the art.

At step S30 a DFT is applied to the samples within a 'window' applied to the sequence of sample frames (for example, a Hann window, as is known in the art). The DFT is performed by a DFT module 500 contained within the processor 400. Each DFT spectrum is processed to yield the energy content of a single window for all frequency bins (as depicted in FIGS. 2a and 2b).

The window is moved over the sequence of sample frames in a series of steps, and the DFT module 500 performs a DFT for the samples within each window. The size of the window is, in some embodiments, the same as the size of a sample frame. Thus, a first window may correspond to the entirety of a first sample frame. A second window may correspond to a portion of the first sample frame, and a portion of a second sample frame, and so on. The ratio between the size of the step and the size of the sample frame is selected in dependence upon the desired overlap between samples in successive windows. If the amount of overlap is increased, for example, the step size is reduced, and the effect is that the number of DFTs which are performed is increased. Consequently, the motion estimation resolution which is possible is increased, referred to herein as 'oversampling'.

At step S40 the frame spectra obtained in S30 are analysed by a motion estimation module 600 contained with the processor 400. In some embodiments, the analysis includes identification of a degree of asymmetry in the energy of each of the plurality of DFT spectra. The analysis includes an analysis of the time-variance of the DFT spectra between successive windows in order to estimate motion over the duration of the window from the fluctuation in energy caused by the reflected tone signal. In some embodiments, the motion estimation includes a measurement of the standard deviation of the energy in each bin over the windows, or a measurement of the energy swing across frames, although it will be appreciated that volatility can be characterised by other suitable means.

In particular, the energy values in the frequency bins bridging the boundary frequency is analysed in step S40 and information characterising motion of the target is extracted by the motion estimation module 600.

As described above, the majority of the information associated with slow motion, that is, of the order of 10 cm/s or less is in the A-pair, with the frequency shift caused by the moving target being of a size that falls within the width of a frequency bin on either side of the boundary frequency. Motion of the target results in fluctuations of the energy content over a sequence of DFT frames visible in one bin of the A-pair compared with the other, depending on whether the motion is towards or away from the microphone 200, enabling the direction of slow motions to be determined.

In some embodiments, motion is estimated in step S40 by the motion estimation module 600 based on an asymmetric fluctuation of the energy in the A-pair. In some embodiments, in step S40, the direction of the motion is estimated based on a comparison of the relative volatility of the A-pair, as described above.

Finally, at step S50 motion estimation, as tracked across the sample windows, is notified by an output module 700. In some embodiments, the output is an acoustic alarm, alert or notification. In other embodiments, the output is visual, or a control signal for a user interface on a mobile device.

Hybrid Technique

As set out above, the boundary technique has unique advantages for observing small Doppler shifts close to the tone frequency, and is thus highly effective for estimation of slow directional movements. This makes it an advantageous technique for real-time motion tracking and displacement measurement, as it produces a highly sensitive, directional response to movements in, for example, the 0-20 cm/s speed range which is important for hand gesture tracking by a smartphone.

For some applications, it may be desirable to increase the number of samples in the frame for the DFT, without changing the sampling frequency, in order to increase the resolution of motion estimation, in terms of the number of frequency bins present in the DFT, and correspondingly, the number of discrete velocities which can be inferred. However, as the number of samples increases, the amount of data in a sample buffer to be processed increases, which has negative implications for system latency, while the motion of a target may become non-uniform over the increased duration of the sample frame. In the context of real time motion tracking discussed above, this can be particularly problematic, as it may be that specific motion modes (e.g. specific speeds or directions) existing for only a portion of a sample frame are not identified. Therefore, there is a need to ensure that improved resolution and accuracy can be achieved without such disadvantages arising.

For a given sampling rate, use of a frame size N that scales with $2^n$ (such as N=1024, 2048, 4096, 8192, etc.) ensures that any boundary frequency with respect to a particular DFT size will correspond to a central frequency (in which the same tone frequency is at the centre of a frequency bin), when a larger DFT is applied to the same pilot tone frequency. This follows from the fact that there are double the number of bins, and that the bin width is halved.

Figure 3:
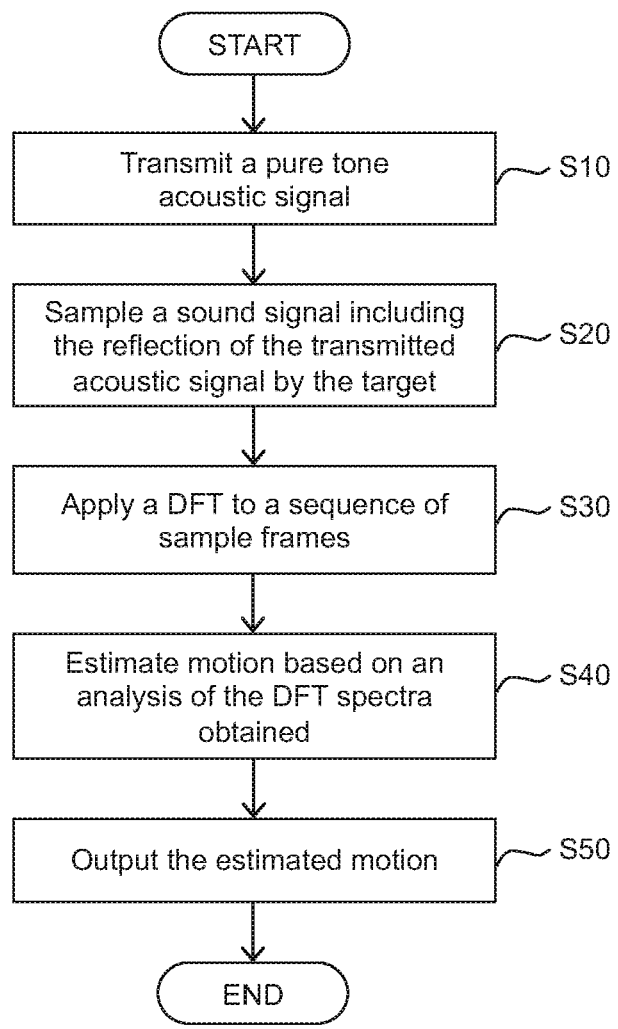
FIG. 3 shows a method for tracking motion of a target according to embodiments of the present invention.

In some embodiments, the method illustrated in FIG. 3 includes an additional layer of analysis in which the pilot tone is simultaneously processed as a boundary frequency in the manner set out above, and also as a central frequency in a larger DFT associated with an increased number of samples.

For example, the hybrid technique is achieved by adopting a DFT configuration in which information from a first DFT size (e.g. using N=2048) in a boundary tone configuration is combined with information from a second DFT size (e.g. using N=4096) in a central tone configuration. Differencing, as described above, is applied to the combined information.

This "hybrid" of boundary and central tones allows the system to achieve the high frequency resolution of the central frequency DFT, and the low latency and slow motion sensitivity of the boundary frequency DFT, simultaneously.

In addition, the manner in which the frequency bins of the two DFTs are combined leads to improved specificity of motion estimation. The realisation of the hybrid technique and the associated advantages are described in detail below.

In general, larger frame sizes such as N=4096 provide a higher resolution frequency analysis, which enables a more detailed analysis of the speed of motion via an increased number of frequency bins. For example, for $f_s$=48 kHz and N=4096 the width of each frequency bin around the tone frequency 18,011.72 Hz will correspond to a range of speeds spanning 22 cm/s between their upper and lower bounds.

For a central tone configuration as associated with a larger DFT in a hybrid technique, Doppler shifts falling within the speed bounds of the central bin which is dominated by the pilot tone energy may be observable as energy fluctuations, but their direction with respect to the microphone cannot be directly observed. In such cases, motion is considered to have an average velocity of 0 cm/s in embodiments of the present invention. The technique also provides high-resolution estimates with reduced sidelobe interference (and hence energy leakage into surrounding bins) for Doppler shifts outside the central bin, and thus provides accurate velocity and displacement measurements for movements faster than 10 cm/s. This technique is therefore useful for enabling distinction between non-directional slow motion within the central bin and fast motion.

The larger frame size associated with the central tone configuration also corresponds to a longer time period of analysis. For example, for $f_s$=48 kHz and N=8192, 171 ms of data is required. After a Hann window is applied to the sequence of sample frames, the energy content of the window, concentrated around the centre of the time window, has a lag (referred to herein as "centroid lag") of at least 87 ms from the point at which the DFT is calculated. This may lead to a perceptible delay between a gesture and an on-screen response derived from estimation of the gesture. Larger frame sizes may therefore be less suitable for real time applications where low latency is required, such as in gaming examples.

Smaller frame sizes such as N=1024 or N=2048 provide lower centroid lag to a minimum of 11 ms or 21 ms to the centre of the analysis window, making such configurations suitable for the real-time motion tracking applications in relation to boundary tone.

Smaller frame sizes provide lower resolution frequency analysis. For example, for $f_s$=48 kHz and N=2048, the width of each frequency bin around the pilot tone frequency 18,011.72 Hz will correspond to a range of speeds spanning 45 cm/s between their upper and lower bounds. This would still provide adequate resolution for typical hand gesture speeds during gaming applications, for example, having speeds of up to 1.2 m/s, which would span across approximately 3 bins on each side of the tone. When N=1024 this resolution is halved, with the width of each frequency bin corresponding to a Doppler shift of a target moving at a speed of approximately 89 cm/s, and thus the ability to distinguish between speeds is reduced.

Figure 5:
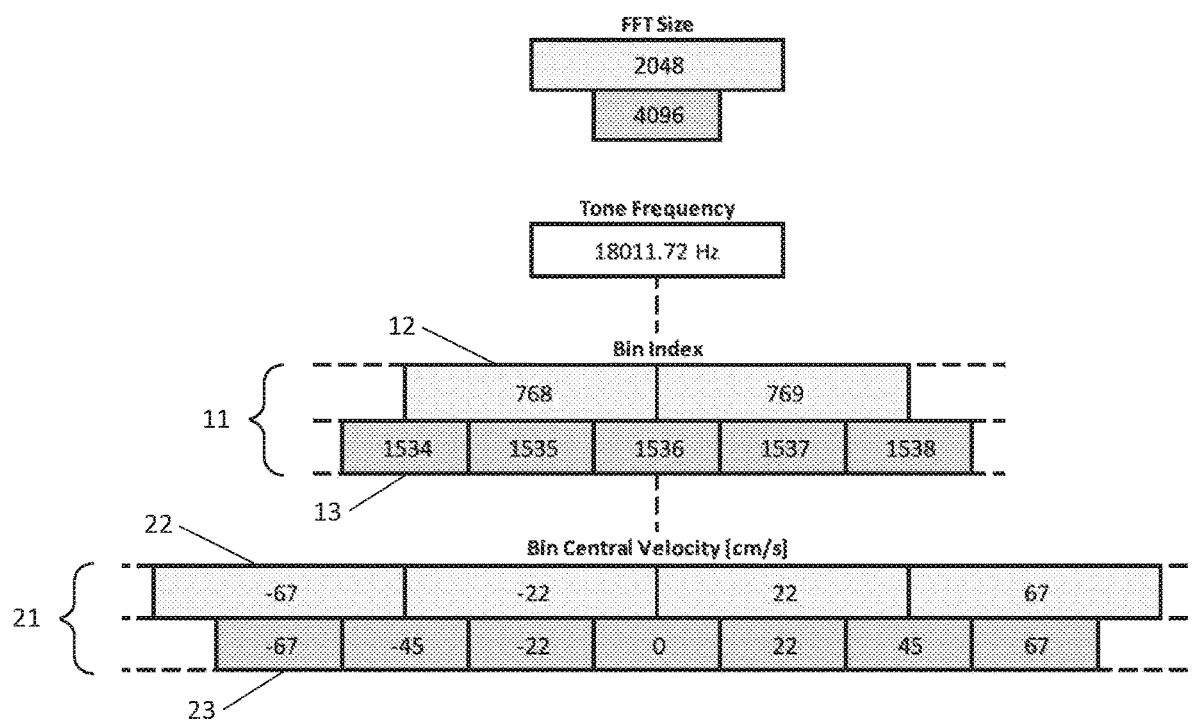
FIG. 5 illustrates the relationship between frequency bins of two DFTs which are combined according to embodiments of the present invention.

FIG. 5 illustrates the relationship between frequency bins of two DFTs which are combined according to embodiments of the present invention. One DFT uses a frame size of 2048 samples, while the other uses a frame size of 4096 samples. Both DFTs are to be applied to the reflection of a pilot tone of frequency 18011.72 Hz, at sampling frequency 48 kHz. This tone represents a boundary frequency for the N=2048 DFT, and a central frequency for the N=4096 DFT.

The frequency bins of the N=2048 DFT (shown in rows 12 and 22) are double the width of the frequency bins of the N=4096 DFT (shown in rows 13 and 23). Additionally, when the frequency bins are represented visually in a "stacked" formation as in FIG. 5, the boundary between two N=2048 DFT bins is aligned with the centre of an N=4096 DFT bin.

FIG. 5 shows the arrangements of bins 11 labelled by index, and also of bins 21 labelled by central velocity.

Significantly, as shown in FIG. 5, the central bin containing the transmitted tone in the N=4096 DFT spans the boundary of the central A-Pair from the N=2048 DFT and has a 0 cm/s central speed for use in the centroid calculations. The hybrid system therefore retains the sensitivity of the boundary configuration, as even small movements create a directional imbalance in the A-Pair bins of the N=2048 DFT, while stability is provided by the N=4096 DFT, and particularly the zero-weighted central bin. The resulting system exhibits high levels of stability and motion sensitivity, and provides highly accurate velocity estimates with only minor increases to latency.

In embodiments of the present invention, energy information from both DFTs is combined to lead to inference of motion in the overlapping range of 0-11 cm/s, which is a much more specific and accurate estimate of motion that would be achieved from either of the DFTs in isolation—this improvement arises due to a combination of the offset of the frequency bins shown in FIG. 5, and their relative sizes, wherein a single bin on the N=2048 DFT spans three different bins of the N=4096 DFT—these overlaps enable additional information to be obtained than would be possible with use of one DFT in isolation. For example, specific techniques of combining energy from two constituent DFTs may be employed, for example, combining energy only from coinciding bins having matching central velocities in the DFTs.

Figure 6A:
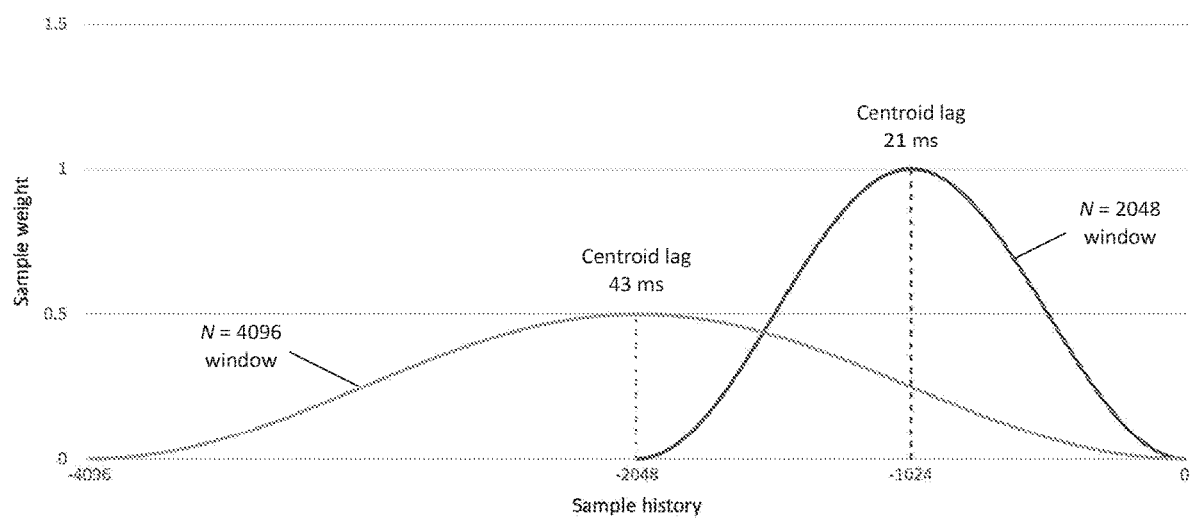
FIG. 6a shows weighted Hann windows for DFTs used in the technique described with reference to FIG. 5.
Figure 6B:
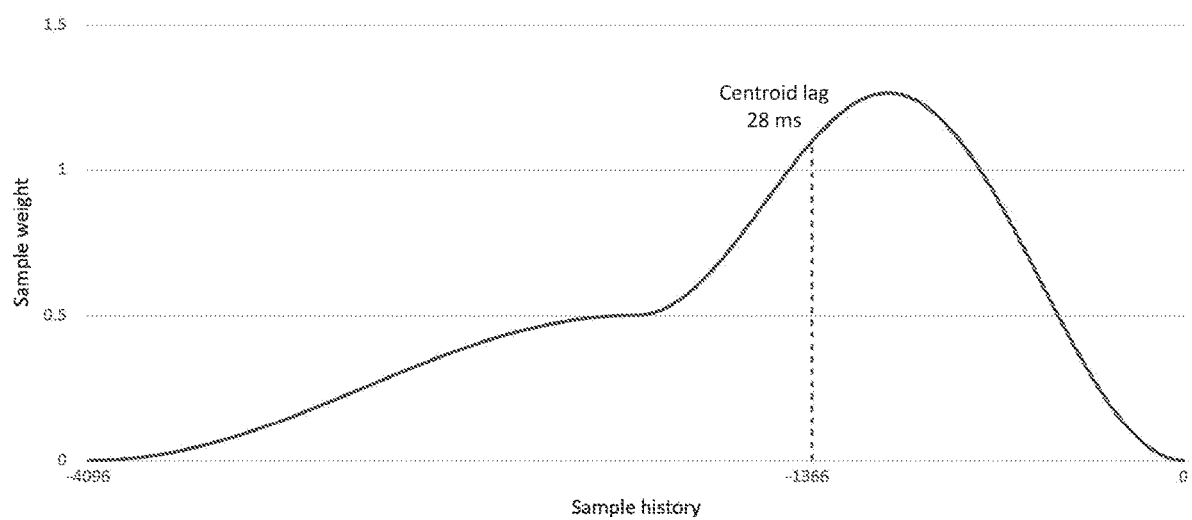

Energy information from the two DFTs is combined to derive what is referred to herein as a composite DFT, which contains as many bins as there are in the N=4096 DFT. The composite DFT can be considered as associated with a composite sample window, as shown in FIG. 6b. The composite window of FIG. 6b is achieved by combining the weighted Hann windows shown in FIG. 6a, in which the N=2048 DFT has a centroid lag of 21 ms and the N=4096 DFT has a centroid lag of 43 ms, and in which the N=4096 window is weighted by 50%. As illustrated in FIG. 6b, the larger N=4096 DFT window is skewed towards the current time by the N=2048 DFT window. The resulting centroid lag is 28 ms in this example.

Since the N=4096 DFT window is double in time duration in comparison with the N=2048 DFT window, it contains, on average, double the amount of energy. As such, when the information from the two DFTs is combined, the energy from the N=4096 DFT is weighted by 50% to that of the N=2048 DFT in some embodiments of the present invention, to avoid biasing the composite DFT to one constituent DFT over the other. In other embodiments of the present invention, different weightings may be applied where there is a desire to bias the composite DFT to one of its constituent DFTs. For example, it may be possible to bias the composite DFT to more recent sample data by increasing the relative weighting of the smaller DFT relative to the larger DFT, in cases where the two DFTs are aligned to the current time. In yet further embodiments, the sample windows for the two DFTs are centred, rather than being aligned to the current time.

As an alternative to combining energy information from two DFTs, in some embodiments, the peak energy is determined in each of the constituent DFTs, and averaged.

Thus, through use of the hybrid technique, the resultant system exhibits greater stability than pure boundary configurations, greater motion sensitivity than central configurations and more accurate velocity estimates overall with only minor increases to latency.

The specific configuration to be used will depend on the application for the motion tracking technique and its requirements for latency and resolution. For example, the boundary technique (e.g. the N=2048 DFT configuration) may be advantageous in applications where the fast possible response is desirable, whilst the hybrid technique (e.g. the N=2048 DFT configuration in combination with the N=4096 DFT configuration) may be more suitable for applications where the highest possible accuracy for speed and displacement measurements is desirable.

Displacement Estimation and Processing

In some embodiments, the method illustrated in FIG. 3, or as modified using the hybrid technique described above, also includes estimation and processing of the displacement of the target, based on the estimated velocity of the motion and the duration of the motion.

Displacement processing methods according to embodiments of the present invention are set out below in conjunction with the apparatus 100 shown in FIG. 4.

As described above, a velocity of the target 51 is estimated and stored in a memory 800 for each window, or frame. The velocity, $v_f$, determined per window is used by motion estimation module 600 to estimate the displacement of the target over the duration, if of that sample window, based on the assumption that the velocity is either constant, or is an average of the true motion, over that duration of the sample window. For a given period of time, T, and for a given sampling rate and frame size, the process of calculating a displacement per window is repeated for the number of windows in the time period T, such that a total displacement s total is calculated by:

$$s_{total} = t_f \cdot \sum_{f=1}^{T/t_f} v_f$$

For example, for $f_s$=48 kHz and a sample frame window size of 512 samples, the number of sample frames analysed per second is 93.75. Thus, for a determined velocity of 10 cm/s in one window, the displacement for that frame is 1 mm.

The resulting displacement estimates for each of the sequence of sample windows are added to provide a cumulative displacement, stored in the memory 800, of the target 51 during detected motion.

The following sections set out a number of displacement processing techniques for use within a variety of contexts according to embodiments of the present invention. Different techniques may be used independently or in combination, according to embodiments of the present invention, depending on the desired application.

1) Displacement Tracking

In some embodiments, the position of a target, such as the hand of a user operating apparatus 100 such as a smartphone, is determined on an ongoing basis based on the cumulative displacement of the user's hand in a particular space. The cumulative displacement, stored in the memory 800, is directional, such that net movement of the user's hand in two directions can be tracked, and a control can be performed by the apparatus 100 triggered accordingly.

Some embodiments, to be described in more detail below, enable emulation of a musical instrument by the apparatus 100. One example is a slide whistle. In this example, the position of the slide in two directions can be determined on an ongoing basis based on the cumulative displacement of a user's hand within the defined displacement range. A sound can be produced by the apparatus 100 on detection of motion representing motion of the slide.

In some embodiments, the space in which movement of the user's hand is detected is a finite space having dimensions which correspond to the screen of the smartphone.

For example, for controlling a sprite on a screen (such as the dolphin displayed on the smartphone screen in FIG. 1), a displacement range may be defined in which motion of the user's hand controls some aspect of the sprite, such as its vertical position on a screen. The displacement range may be similar or proportional to the height of the smartphone screen, such that there is correspondence between the distance moved by the sprite on the screen and the cumulative displacement of the user's hand with respect to the microphone 200. For example, a movement of 5 cm towards the microphone 200 by the user's hand would cause the sprite to move upwards on the screen by 5 cm. In this way, a strong connection, in the way of visual feedback, is created between the movement of the user and the movement of the sprite.

In some embodiments, displacement of the user's hand outside of a defined displacement range is disregarded on the basis of cap and floor logic implemented by motion estimation module 600. For example, this may prevent the sprite from moving outside of the bounds of the game area visible on the screen by ignoring movement of a user's hand away from the microphone 200 which exceeds a predefined maximum displacement. By capping the value of the cumulative displacement at the point that the user's hand leaves the defined displacement range, subsequent movement of the user's hand back towards the microphone 200 may cause the sprite to immediately resume movement in the corresponding direction within the game area, without any requirement to retrace the previous displacement outside of the displacement range. For example, if the initial position of the sprite is 5 cm above the floor of the defined displacement range, a 10 cm displacement of the user's hand away from the microphone 200 would cause the sprite to move downwards 5 cm to the floor and then stop, with the additional 5 cm moved by the user's hand being ignored. An immediate 5 cm displacement of the user's hand back towards the microphone 200 would cause the sprite to move 5 cm upwards to its initial position of 5 cm above the floor.

In some embodiments, the cumulative displacement is reset to zero at the point that the displacement of the user's hand exceeds the defined displacement range, enabling a wrapping effect to be associated with movement outside the defined displacement range. For example, if a movement of the user's hand through a displacement range of 10 cm is defined to correspond to rotation of a sprite through 360° degrees, additional displacement outside of this range may cause continued rotation of the sprite. In more detail, the cumulative displacement is reset to zero at the point that the user's hand completes a 10 cm displacement, such that an additional 5 cm displacement of the user's hand causes the sprite to rotate by an additional 180°.

Use of the boundary frequency makes the system highly sensitive to movements having a physical range comparable to the size of the device to be controlled, such as a typical smartphone having a screen size of approximately 15 cm. For example, in cases where a sample frame contains 4096 samples and a boundary tone frequency in the low audibility range of 18-20 kHz is used, movements up to 20 cm/s would cause a frequency shift of a size falling within that of a frequency bin adjacent to the boundary tone (i.e. within in the A-pair). Detection of slow, directional movements within a displacement range, as described above, is thus greatly enhanced by use of a boundary frequency for the pilot tone.

2) Impulse Gestures

In some embodiments, the displacement of a target is tracked over a series of discrete short time periods. If a time period passes in which no motion is detected, cumulative displacement is reset to zero. Motion in a subsequent time period will contribute to the cumulative displacement. Motion can therefore be interpreted as a discrete 'impulse' gesture, bounded by records of zero cumulative displacement, and distinct gestures, such as hand movements, can each trigger new actions from a consistent baseline of zero cumulative displacement.

In some embodiments, information about the cumulative displacement within a particular time period is used to modify a user control for the apparatus 100, such as modifying the magnitude of an action triggered by a gesture. In an example in which the apparatus 100 simulates and displays water waves, created as a result of a gesture in which the user's hand moves towards the microphone 200, the size of a wave may be determined by the size of the displacement of the user's hand towards the microphone 200 during the 0.5 s preceding the wave's creation on completion of the gesture, whereby a more extensive gesture causes a larger wave.

In some embodiments, the user may configure the apparatus 100 such that it responds only to gestures detected in a particular direction. In the wave simulator example, the creation of a wave may be triggered only by movement of a user's hand towards the microphone 200, with movement away from the microphone 200 having no effect. This allows the user to reset their hand to a comfortable position without triggering an action/control.

In some embodiments, the user may configure the apparatus 100 such that it stores displacement corresponding to movement of a user's hand towards the microphone 200 only, and disregards displacement of the user's hand in the opposite direction. In this way, only gestures towards the microphone 200 contribute to the stored cumulative displacement, and a sequence of gestures may all contribute to an overall target value of cumulative displacement. For example, in a race simulation game, a game character may be moved towards a finish line in increments corresponding to repeated gestures towards the microphone 200, whilst any reverse movement between gestures has no effect on the character's position. In more detail, if the finish line corresponds to completion of total displacement of 100 cm, a sequence of ten gestures each corresponding to a displacement of 10 cm towards the microphone 200 would cause the game character to reach the finish line. A sequence of gestures may include any number of gestures of varying values of displacement summing to 100 cm.

3) Threshold Displacements

In contrast to identification of gestures based on tracking of displacement over discrete time periods, in other embodiments of the present invention it is possible to identify gestures made by the user's hand based on continuous and cumulative tracking of the user's displacement. A particular gesture made by the user's hand may correspond to a specific displacement occurring over a period of time, which may in turn correspond to a particular control for a user interface on a mobile device. In such embodiments, a control is triggered based on a minimum or threshold value of displacement, such that actions are not triggered accidentally by small movements.

In more detail, a particular user control corresponding to a particular gesture is triggered at the point that a virtual threshold position within a particular motion displacement is crossed. For example, in the case of a gesture based on linear motion towards or away from the microphone 200, an event may be triggered when the user's hand crosses a virtual "trigger" position.

For example, the apparatus 100 may be implemented as a gaming device in some embodiments of the present invention. Here, a particular gesture may enable contactless interaction with the game, via provision of a particular command to a game character. For example, a trigger event may occur at a displacement of 5 cm in a predetermined direction occurring over 0.5 s and trigger a "jump" command, whilst a displacement of 5 cm in the opposite direction occurring over 0.5 s may trigger a "duck" command.

In some embodiments, a single trigger event corresponds to a single instance of a control for the apparatus 100 being performed. In such embodiments, it may only be possible to trigger the control again once it is determined that the motion associated with the trigger event has been reversed, for example a user's hand has moved in the opposite direction by a predetermined displacement.

In other embodiments, it may only be possible to trigger a new control once a predetermined time has elapsed after the first trigger event has occurred, the predetermined time based on the assumption that a user is again in a position to input a new gesture.

In some embodiments, a single trigger event causes a control to be performed repeatedly for the entire duration of time that the user's hand remains beyond the threshold. For example, if it is determined that the user's hand remains beyond the threshold after 0.1 s has elapsed since the user's hand first crossed the threshold, the apparatus 100 may perform a sequence of operations, or a prolonged instance of a single operation, until it is determined that the crossing event has been reversed and the user's hand has moved back below the threshold.

In such embodiments, the user may configure the apparatus 100 to respond to certain gestures with a particular control. For example, in a golf simulation game, the user may set up the device such that particular displacements correspond to particular backswing lengths for a variety of strokes. The size of the required displacements may differ depending on the environment in which such a game is played and between different users of the gaming device, and so the device may be configured accordingly. The configuration may be performed via a settings interface on an application implemented on a mobile phone, for example, which embodies the apparatus 100, in which the settings interface provides input to the processor 400 based on input to the user interface 900.

In some embodiments, continued measurement of displacement beyond the threshold after the occurrence of a crossing event provides additional information which is used to modify a user control for the apparatus 100.

For example, if the apparatus 100 is implemented as the gaming device described above, a threshold displacement of 5 cm towards the microphone 200 in 0.5 s commands a game character to "jump" to a certain height. Once this threshold is crossed, any additional displacement may modify the jump, such as by increasing the height of the jump by a predetermined amount for every additional centimetre of displacement measured beyond the threshold.

In addition to enhancing the control gestures which are available to the user, there is an advantage that responsiveness to the gesture can be improved, and latency reduced, since it is not necessary to wait until an entire gesture is complete before processing of the gesture begins. Such latency minimisation is particularly beneficial in real-time control used in a gaming environment, for example, where the initiation of a character's jump action can occur at a time closely relating to the timing of a crossing event in a user's gesture, without the delay that would be caused by the gaming software calculating a landing position prior to the character jumping.

4) Motion Profile

As an extension to the technique described above, in which a control is triggered based on a gesture corresponding to a threshold value of displacement, in some embodiments of the present invention, a displacement-time profile of the gesture within a particular displacement range provides information used to modify a user control for the apparatus 100.

For example, in a golf simulation game, a displacement of a user's hand of 10 cm towards the microphone 200 may trigger an action to strike a ball. The time taken to achieve the required displacement of 10 cm (i.e. the average speed) may determine the power of the strike, such that a faster motion causes the ball to travel further. Additionally, the stability of the ball's flight may be determined by the path taken by the user's hand motion during the time taken to achieve the required displacement, such that a consistent hand speed may cause the ball to travel in a straight line, whilst an inconsistent hand speed may cause the ball to travel in a less stable manner.

5) Inflection Points

In some embodiments of the present invention, the apparatus 100 may be implemented as a musical instrument. For example, if the apparatus 100 is implementing a guitar, different gestures may control the apparatus 100 to produce different sounds.

Figure 7:
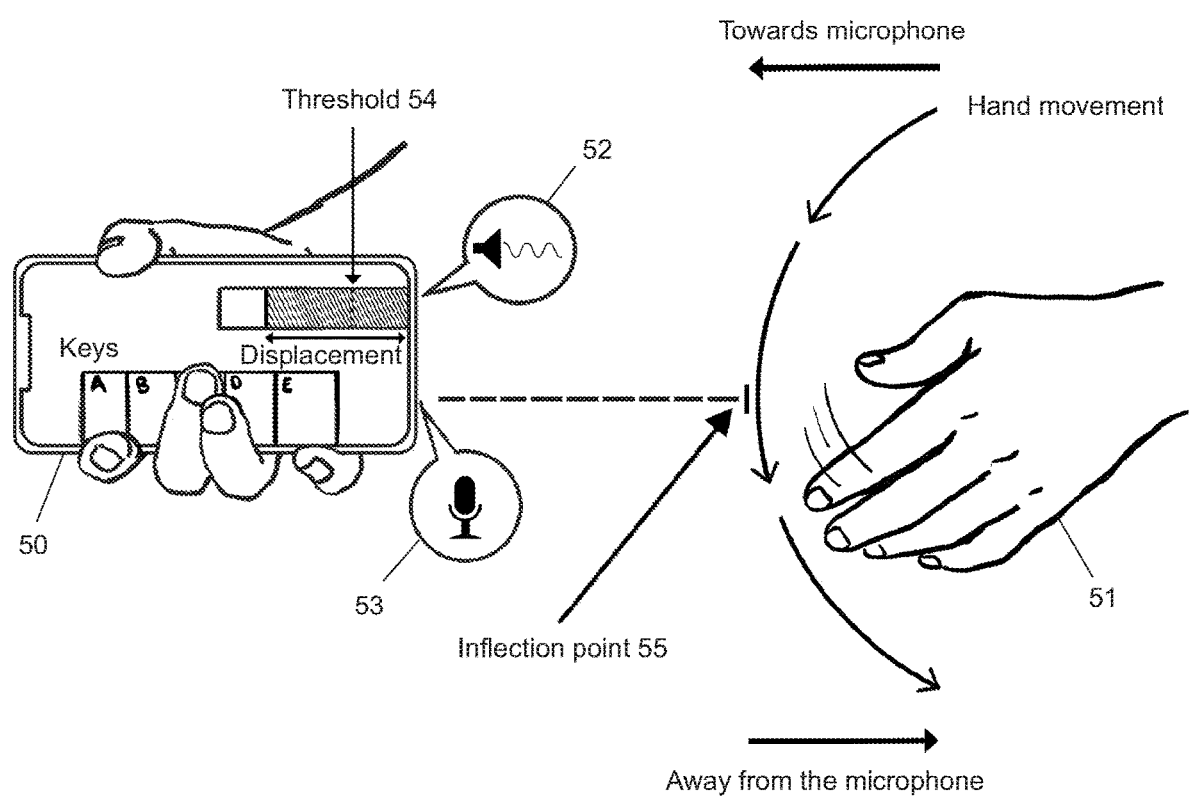
FIG. 7 shows an example of a device which may be used for processing displacement of a target according to embodiments of the present invention.

FIG. 7 illustrates a device 50 which may be used for estimating displacement of a target 51, comprising a speaker 52 and a microphone 53, according to an embodiment of the present invention. In the present embodiment, the device 50 is a smartphone enabling simulation of a guitar, and the target 51 is a user's hand making gestures to control the smartphone to produce sounds. The device 50 comprises processing means (not shown) configured to control the speaker 52 and the microphone 53, and to execute computer-readable instructions to perform the methods described below, in order to estimate displacement of the target 51. The device 50 may correspond to an example of the apparatus 100 shown in FIG. 4, with speaker 52 corresponding to speaker 300 and microphone 53 corresponding to microphone 200. As such, reference signs of like components illustrated in FIGS. 4 and 5 are considered to be interchangeable.

In the guitar example, a displacement of 5 cm in a particular direction occurring over 0.3 s may correspond to a "strum", and a displacement of 1 cm occurring over 0.2 s may correspond to a "pluck", in accordance with the techniques described above. In such cases, the pitch of the note(s) being played can be determined by interaction with user controls on an application running on the apparatus 100. For example, an application may comprise a graphical user interface (GUI) to be displayed by the apparatus 100, the GUI comprising controls for selection of one or more keys or strings, as shown on the mobile device 50 in FIG. 7. A sound corresponding to the selected keys or strings is produced on determination of a strum or a pluck event.

In some embodiments, a particular user control corresponding to a particular gesture is triggered at the point that the velocity of the user's hand switches direction (as represented by the horizontal arrows in FIG. 7), referred to herein as an "inflection point". This is shown in FIG. 7 in conjunction with an example in which the device simulates a guitar. In FIG. 7, the inflection point 55 is shown at a position which approximately corresponds to the position of a virtual string extending from the microphone 53. As the user's hand crosses the virtual string a sound is produced, as would be the case when playing a physical guitar.

In this example, a GUI displayed by the device 50 may include a visual representation of the user's current cumulative displacement with respect to the microphone 53, in real time, relative to a predetermined threshold displacement 54. This may be in the form of a "bar" showing cumulative net displacement of the user's hand 51 towards the microphone 53, for example, over a period of time, as shown on the mobile device 50 in FIG. 7. The bar changes in length in real time, as the user's hand moves towards or away from the microphone 53, providing visual feedback of the interpretation of the user's hand movement by the device 50.

While the inflection point 55 represents a point of triggering a sound, it is possible to make use of the above-described configurations in which a threshold displacement 54 of the user's hand 51 is required over a predetermined time period in order for inflection of the user's hand 51 to be processed. The configuration of such a threshold displacement 54 ensures that sound is not triggered by small, unintentional gestures, and is triggered only by larger, deliberate movements.

The predetermined triggering displacement is represented by a threshold displacement 54, indicated by a marker overlaid on the bar. The threshold 54 represents a minimum displacement of the user's hand 51 required in order for a strum or a pluck to be processed when the user's hand 51 crosses the inflection point 55.

In some embodiments, the user can calibrate the apparatus according to a particular environment or a desired playing style by manually adjusting the threshold 54 via input to the device 50. This may be performed via an interaction with the GUI, such as by dragging the position of the threshold marker to a new position on the displayed bar.

Although FIG. 7 shows inflection of a user's hand 51 moving substantially across a virtual string, it is also possible to consider alternative musical instruments in which movement of the user's hand is substantially along a direction towards or away from a microphone. The same principles of operation apply to such embodiments.

In some embodiments, the inflection point 55 corresponds to a detected occurrence of zero velocity of the user's hand, subject to presence of a threshold displacement as described above, in which a positive (or negative) velocity towards (or away from) the microphone 300 is determined to have become zero. For example, in some embodiments, the apparatus 100 may simulate a drum, and simulation of the striking of the drum may be triggered at the point when the user's hand is determined to have moved towards the microphone 200 through a threshold displacement corresponding to a strum gesture (such as 5 cm in 0.3 s), and then stopped.

An inflection event may be considered as a trigger to take readings of the displacement associated with a gesture, over the period of time preceding the inflection event during which the gesture occurred. Based on this measurement, it can be determined whether or not a threshold value of displacement has been achieved; if so, a sound may be triggered. It is also possible to determine the length of time taken for the threshold value to be achieved, as well as to determine whether and to what extent the threshold value has been exceeded. This information may be used to modify the sound produced by the apparatus 100, as will be described below.

In some embodiments, the magnitude of the displacement of the user's hand 51 prior to registration of an inflection event is used to modify a sound produced by the apparatus 100. For example, in musical instrument implementations, a bigger movement towards the microphone 53 by the user's hand 51 may cause the device 50 to produce a louder sound than that caused a smaller movement.

The description of the above embodiments makes clear that it is possible to use multiple displacement-measurement techniques within the same context, such as the simulation of a guitar. The use of different techniques, in combination, may enable a number of different control effects to be achieved, enhancing the simulation of the overall embodiment. For example, for a configuration simulating a violin, an inflection event may correspond to a sharp 'plucking' of a string, whereas, a threshold event may be represented as a longer sound corresponding to use of a bow.

Use of Multiple Pilot Tones

In some embodiments, the apparatus 100 comprises a plurality of speakers arranged to transmit a respective plurality of pilot tones in different directions, which are detected by a plurality of microphones which may be substantially co-located with each speaker, but which, in other embodiments, may be arranged to detect sound from speakers which are displaced from the microphones. Additionally, in some embodiments, fine-tuning of such multiple-tone embodiments is possible through configuration of the motion estimation to be performed in each direction.

In some embodiments, a single speaker 300 is configured to transmit a superposition of multiple pilot tones, at least one of which is at the boundary of a respective pair of adjacent frequency bins in the DFT. The single speaker may, in other embodiments transmit at least one pilot tone for the purposes of motion detection, but also transmit sound not used for motion detection, such as background music or sound effects.

Boundary Tone for Displacement Estimation

As described above, use of a boundary frequency for the tone transmitted by speaker 300 enables estimation of motion with improved accuracy, sensitivity and specificity. Using the method described above in FIG. 3, motions of a user towards or away from the microphone 200 have a clear, asymmetric effect on the energy content of the A-pair, thus enabling the direction of motion to be readily determined. This has clear benefits for the musical instrument and gaming implementations of apparatus 100 in particular, or other embodiments which require the apparatus to be highly responsive to directionality for successful identification of gestures.

Use of the boundary frequency makes the system highly sensitive to movements having a physical range comparable to the size of the device to be controlled, such as a typical smartphone having a screen size of approximately 15 cm. The sensitivity of the boundary tone technique makes the apparatus 100 very responsive to slow movements, thus enabling fine control of the apparatus and providing an extensive range of motion to be detected. The ability to detect low velocities enables precise measurement of displacement, in the manner described above.

In addition, as described previously, the symmetry of the bins about the boundary tone enables highly accurate detection by the apparatus 100 of zero velocity in the case of no motion, which has particular advantages in the identification of the end of a gesture in the gesture-based embodiments, and the identification of directional velocity, and hence displacement, for the inflection-based embodiments.

The symmetry of the bins about the boundary tone also enables the system to function optimally in the presence of external noises, as energy fluctuations caused by external noises have a more symmetric impact on the energy content of the A-pair compared with the asymmetric energy fluctuations caused by movements (as described above with reference to FIGS. 2a and 2b). This is beneficial for sleep-tracking embodiments since it enables lower tone volumes to be used whilst filtering external noises.

Motion Estimation Apparatus

Figure 4:
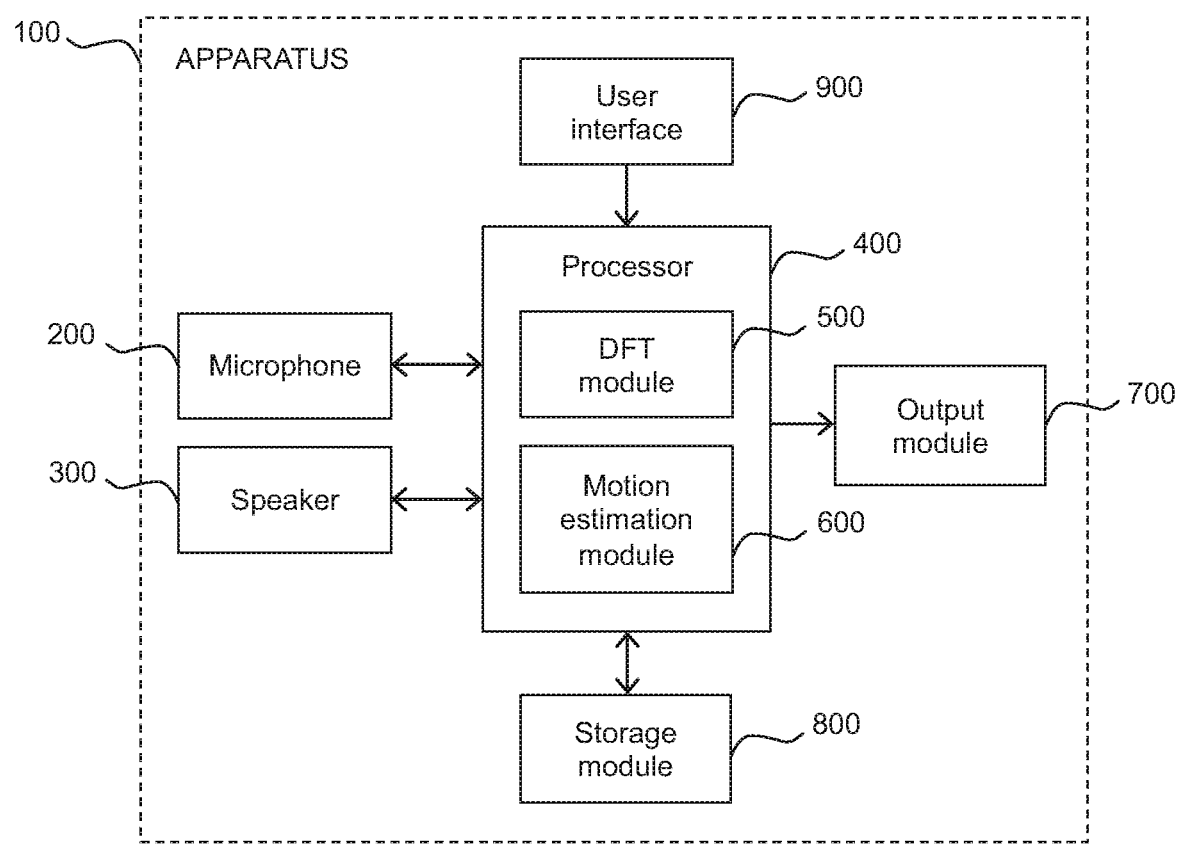
FIG. 4 illustrates an apparatus for performing the method illustrated in FIG. 3, according to embodiments of the present invention.

The components illustrated in FIG. 4 represent a stand-alone apparatus in some embodiments, in which each component is specifically configured to implement the method of FIG. 3. In other embodiments, the components are part of a device such as a smartphone or tablet on which the method of FIG. 3 is implemented via execution of computer-readable instructions. For example, processor 400 may represent a section of computer-readable instructions or code to be executed by a processor or controller of a device supporting the method of FIG. 3. Similarly, the DFT module 500 and motion estimation module 600 may represent execution of further computer-readable instructions. The output module 700 may correspond to display, audio output or communication signal output components of the device, while the microphone 200 and speaker 300 may be those already on-board the device. In yet further embodiments, the microphone and speaker may be off-the-shelf components coupled to a personal computer. Additionally, the apparatus comprises a storage module 800 or memory, for storing cumulative displacement as described above, motion estimation results, and may, in some embodiments, store the computer-readable instructions described above. A user interface module 900 is provided to enable interaction with the apparatus by a user, and may implement a GUI or button-based interface for provision of controls or input of configuration settings.

Although the DFT module 500 and motion estimation module 600 are shown as separate components in FIG. 4 they may, in alternative embodiments, be considered as a single component represented by processor 400. In yet further embodiments, such a single component may be separate from, or contained within a central processing unit of the device embodying FIG. 4.

The specific configuration to be used will depend on the application for the motion estimation technique, and examples of such applications are described below. It will also be appreciated that the components of FIG. 4 may be embodied in hardware, software, or a combination of both.

One example is where motion estimation is performed as part of sleep tracking analysis. In such embodiments, the method described in FIG. 3 can be performed by execution of computer-readable instructions downloaded or installed as a software application on a mobile phone. In this example, the processing components described in connection with the FIG. 4 may correspond to functional modules, such as sections of software code, executed by one or more processors in the mobile phone. It will be appreciated that other mobile devices, such as tablets, or personal computers may also support the apparatus shown in FIG. 4.

The speaker of the mobile phone transmits the pilot tone and the microphone of the mobile phone receives the signal reflected from the user. The application running on the mobile phone performs DFT analysis periodically through the night, for example, and may either track motion for output to an analysis engine, or for output to a dashboard for analysis by a user, or for triggering a smart alarm to wake a user when determined to be in light sleep based on detected motion within a predetermined time range or period. The inaudible transmission signal ensures that the user experiences no discomfort while sleeping.

Use of a boundary frequency also enables use of a low volume pilot tone without compromising the sensitivity of motion detection. The sensitivity that is achievable using the method of embodiments of the present invention means there is no need to increase the volume of the pilot tone to enhance performance, thereby avoiding associated negative implications for power consumption. This would be highly desirable in the context of sleep tracking analysis using a mobile phone, to conserve battery during prolonged use of the mobile phone overnight. The use of a boundary frequency tone enables slow motion to be detected with an inaudible signal.

As described above, in some embodiments, the apparatus comprises a plurality of speakers placed so as to transmit a superposition of pilot tones in different directions. A respective pilot tone is emitted from each speaker, and detected by a respective microphone substantially co-located with each speaker on the apparatus. The frequencies of each pilot tone are different so as to enable the processor 400 to process the DFT and detect motion from each received signal in parallel. Each transmitted pilot tone has a different boundary frequency, although in some embodiments, it is only necessary for at least one of the transmitted tones to have a boundary frequency. It is further possible to transmit music or other sound effects in addition to one or more pilot tones.

In the case of a two speaker/two microphone arrangement, for example, this creates a two-dimensional space in which it is possible to detect motion, for example to the left and to the right, as well as towards or away with respect to the apparatus. For example, the apparatus may be a smartphone having a first speaker arranged in a direction perpendicular to the phone's surface, and a second speaker arranged in a direction parallel to the phone's surface. Such an arrangement may be particularly advantageous in a situation where motion detection is used as part of the user interface control on the smartphone through gestures made by a user's hand.

The user interface described above can, in some embodiments, enable fine-tuning of such multiple-tone embodiments through enabling selection of each frequency, and configuration of the motion detection to be performed in each direction. Motion detection in one direction may take priority over motion detection in another direction, such that a higher sensitivity is enabled in one direction over another. Such sensitivity can be implemented by the DFT module 500 applying different thresholds to determine high volatilities in the DFTs associated with the respective received signals, so that larger fluctuations might be required to be indicative of motion in one direction rather than another. Such control can take into account background noise so as not to configure the system to be over-sensitive in any particular direction. In alternative embodiments, motion in one direction may be selectively disregarded—this can apply both to selective deactivation of a particular speaker/microphone combination, or to selective disregarding of motion detected by the motion estimation module 600 in one of the two shift directions with respect to the boundary frequency in the DFT spectrum.

As above, it will be appreciated that the apparatus of FIG. 4 can be embodied in a number of different devices for a number of applications. A sleep-tracking embodiment is described above, in which the apparatus may represent components of a mobile phone configured to run an application containing computer-readable instructions which, when executed, cause the method of FIG. 3 to be performed. In alternative embodiments, the sleep-tracking embodiment may be implemented in a standalone apparatus to be positioned next to a user's bed, the apparatus containing the microphone 200 and speaker 300 and the processor 400.

In further embodiments, the method of FIG. 3 is used as part of the control of a user interface on a mobile device, tablet or portable gaming device, in which gestures by a user's hand, for example, control one or more aspects of a user interface objects, such as a cursor, scroll bar, or game character. An example environment for such an embodiment is illustrated in FIG. 1. In these embodiments the effect of motion detection is represented visually on the screen, and in addition to controlling an interface, generation of visual effects may be performed. As an alternative to interface control, device control such as the control of a particular operating parameter (e.g. volume, or brightness) may be performed.

Directionality of target motion may be measured towards or away from the microphone 200 in such embodiments, and it is also possible to configure the user interface such that it responds only to motion detected in one of these two directions (for example, towards the microphone). Among other implementations, this provides the user with the ability to make repetitive unidirectional control gestures, such as scrolling.

The fact that slow motion can be detected by embodiments of the present invention leads to detection of gestures having a physical range of an order of magnitude comparable to the size of the device to be controlled.

In further embodiments, the method of FIG. 3 is performed by a security apparatus configured to trigger an alarm in response to detection of motion. The security apparatus may be a standalone device comprising an in-built alarm, or a connection to a remote alarm system, or may be embodied in a mobile phone or other portable device linked to the alarm system.

In each embodiment, the nature of the output provided by output module 700 is dependent on the specific context in which the embodiment operates. In some embodiments, the output module represents a display unit which illustrates detected motion visually so that a user can take particular action. In other embodiments, the output module represents an alarm, whether sound and/or light, or some other notification such as an email or message, or operating system notification. In yet further embodiments, the output module represents the packaging of data representing motion detection, whether instantaneous, or whether historical, measured over a period of time, which can be synchronised with an external device such as a personal computer, tablet, mobile phone or server, including cloud-based devices, in order for motion data to be uploaded and analysed further by such an external device. In the context of a sleep analysis embodiment, for example, an external sleep analysis engine may pull in motion data from the output module 700 in order to perform more detailed sleep phase analysis.

Modifications

In some embodiments, it is possible to select a boundary frequency for the pilot tone based on the nature of the environment in which the apparatus is to be used. This is determined by placing the apparatus 100 in the environment and analysing a sound signal sampled by the microphone 200, including any background or environmental noise present at a particular frequency (for example, noise generated by a fan in a particular room). The analysis is performed by the DFT module 500 generating a DFT of signals received by the microphone 200 so as to identify particular spikes in the spectrum representing noise having specific frequency components. The processor 400 then applies the expressions set out above using a target tone frequency which is far away from the frequency of any identified noise. This process ensures that the analysis of the energy of the DFT in the A-pair frequency bins is not affected by the background noise.

In embodiments in which the calibration routine is not performed, the boundary frequency is either fixed, hard-wired into computer-readable instructions which are executed by the processor 400, or can be configured by the user via an interface (not shown) on the apparatus 100. The interface may be a settings interface on an application implemented on a mobile phone, for example, and provides input to the processor 400.

More generally, such a user interface may enable, in some embodiments, configuration of a number of other parameters including, but not limited to, energy/volume of the pilot tone, timing of periodicity of pilot tone, sampling frequency, microphone sensitivity, and any output format settings.

Embodiments of the present invention address the effect of background noise on motion detection, through use of a pilot tone having a boundary frequency, which enables asymmetric fluctuations caused by genuine motions to be clearly distinguished from any global change in the energy content of the bins caused by external noises (as described above with reference to FIGS. 2a and 2b).

The effect of noise can be further reduced by the motion estimation module 600 discarding DFT spectra which are indicative of energy in both frequency bins of the A-pair having simultaneously increased or decreased beyond a threshold level, relative to previous DFT spectra. Such an indication does not represent motion, but indicates fluctuations due to noise. By discarding such spectra, it is ensured that the only data to be processed by the motion estimation module 600 is that which indicates motion due to the presence of asymmetry in the sense of the energy change in the A-pair bins. For quiet environments, this technique can be particularly beneficial. The filtering of data representing noise also reduces the processing burden applied to the motion estimation module 600, further leading to power saving and calculation efficiency benefits.

In some embodiments, it is possible for the DFT module 500 to perform a DFT which contains only information in a limited frequency range around the boundary frequency. This is achieved by control of DFT coefficients in the algorithm characterising the operation of the DFT module 500. This has the effect of simplifying the DFT process and reducing the data to be analysed by the motion estimation module 600, since information in the DFT spectra which is outside of the central bin pairs may be redundant. Embodiments in which motion is to be detected on a rolling basis, for example as a 'background process' running in parallel with other applications on a smartphone, will also take particular advantage of these benefits.

In some embodiments, it is possible to select a volume for the pilot tone based on the nature of the environment in which the apparatus 100 is to be used, and the power of the speakers to be used. This is determined by transmitting a test tone via the speaker 300 into the environment and analysing a sound signal sampled by the microphone 200, including the reflection of the transmitted test tone, by the environment. Depending on the energy received, relative to environmental noise, the volume of the tone can be controlled accordingly. The volume can also be set manually via a user interface, based on one of a number of predetermined operating environments, speaker types, duration of use, or the power source of the apparatus (for example, mains power or a battery).

In some embodiments, analysis is performed within step S40 of FIG. 3 on what are referred to herein as "secondary bins" (shown in FIGS. 2a and 2b as f(n−5) . . . f(n−1) and f(n+2) . . . f(n+6)) outside of the central A-pair. For simplicity, f(n+2) may be referred to as a B-bin, f(n+3) may be referred to as a C-bin, and so on. Inclusion of these secondary bins in the analysis enables information characterising faster movements to be extracted (for example, of the order of 50 cm/s or more) which cause Doppler shifts to exceed the width of the A-pair bins in the DFT. It is possible to determine velocity of motion based on the size of the frequency shift caused by the motion, in accordance with the equations set out above.

For example, if the energy peak of the reflected signal is identified in C-bin f(n+3), analysis may be performed on a set of bins about the peak, such as a group containing the neighbouring E-bin, D-bin, B-bin and A-bin surrounding the C-bin, rather than analysing bins on either side of the boundary tone. In some embodiments, the analysis involves calculation of a centroid of the energy distributed across the relevant set of bins. In the case of an asymmetric peak in particular, calculation of the centroid provides an accurate measurement of the displacement of the user during a detected motion.

It will be appreciated that a variety of implementations will fall within the scope of the claims, the specific implementation depending on at least the desired nature of the motion detection result, the desired motion sensitivity, the motion detection environment, the anticipated motion of the target, and the available hardware. Compatible functions of the embodiments described above may therefore be combined as required in order to form new embodiments, as desired for a particular application.

The invention claimed is:

1. An apparatus for tracking motion of a target, comprising:
    a speaker configured to transmit a pure tone acoustic signal;
    a microphone configured to sample a signal reflected by a target ensonified by the transmitted pure tone acoustic signal; and
    processor configured to:
        control the speaker and the microphone;
        estimate motion of the target based on analysis of a plurality of Discrete Fourier Transformations (DFTs) of the sampled signal, wherein the plurality of DFTs are represented by a plurality of energy values in each of a respective plurality of frequency bins, such that the analysis is based on a time-variance of energy values in at least a pair of frequency bins centered around the frequency of the transmitted pure tone acoustic signal, and any DFT of the plurality of DFTs is configured such that either:
        a boundary between two adjacent frequency bins is at the frequency of the transmitted pure tone acoustic signal; or
        the center of a frequency bin is at the frequency of the transmitted pure tone acoustic signal;
    the apparatus further comprising output means configured to output the estimated motion of the target.

2. The apparatus of claim 1, wherein the pair of frequency bins centered around the frequency of the transmitted pure tone acoustic signal are adjacent to each other, and the boundary between the two adjacent frequency bins is at the frequency of the transmitted pure tone acoustic signal,
    wherein estimating motion of the target further comprises determining a direction of movement of the target based on a comparison of the time-variance of energy values in the adjacent frequency bins.

3. The apparatus of claim 1, wherein the pair of frequency bins centered around the frequency of the transmitted pure tone acoustic signal are separated by, and are adjacent to, a frequency bin comprising the frequency of the transmitted pure tone acoustic signal,
    wherein estimating motion of the target further comprises determining a direction of movement of the target based on a comparison of the time-variance of energy values in the pair of frequency bins.

4. The apparatus of claim 1, wherein the analysis of Discrete Fourier Transformation of the sampled signal comprises:
    performing a first DFT of the sampled signal, wherein the first DFT is based on a first number of samples;
    performing a second DFT of the sampled signal, wherein the second DFT is based on a second number of samples which is at least double the first number of samples;
    estimating motion of the target based on analysis of a combination of the first DFT and the second DFT;
    wherein the boundary between two adjacent frequency bins of the first DFT is at the frequency of the transmitted pure tone acoustic signal; and
    wherein the center of a frequency bin of the second DFT is at the frequency of the transmitted pure tone acoustic signal frequency of the transmitted pure tone acoustic signal.

5. The apparatus of claim 1, wherein the processor is further configured to infer velocity of motion of the target based on a calculation of a centroid of differential energy values, in the frequency domain, between sequential DFTs.

6. The apparatus of claim 1, wherein the processor is further configured to:
    infer velocity of motion of the target based on a calculation of a centroid of differential energy values, in the frequency domain, between sequential DFTs; and
    estimate displacement of the target from the inferred velocity of motion of the target and a duration of the estimated motion.

7. The apparatus of claim 6, wherein the output means is configured to output a sound according to one or more gestures determined from the estimated motion of the target, wherein the apparatus is a musical instrument.

8. The apparatus of claim 6, wherein the apparatus is a gaming apparatus and the processor is configured to control a game character according to one or more gestures determined from the estimated motion of the target.

9. The apparatus of claim 8, wherein the processor is arranged to control a user interface in accordance with one or more gestures estimated from the estimated motion.

10. The apparatus of claim 8, wherein:
    the processor is arranged to control a user interface in accordance with one or more gestures estimated from the estimated motion; and the one or more gestures are estimated from the estimated motion in one predetermined direction.

11. The apparatus of claim 1, wherein the apparatus is a sleep-tracking apparatus comprising a means for performing sleep analysis based on the estimated motion of the target.

12. The apparatus of claim 1, wherein:
the apparatus is a sleep-tracking apparatus;
the sleep-tracking apparatus comprises a means for performing sleep analysis is based on the estimated motion of the target; and
the output means is configured to output an alarm within a predetermined time of the means for performing sleep analysis determining arousal or light sleep of the target.

13. The apparatus of claim 1, wherein the output means is configured to output an alarm or notification according to an estimated occurrence of motion.

14. The apparatus of claim 13, wherein the output means is configured to further display a visual representation of the estimated motion of the target.

15. The apparatus of claim 1, wherein the processor is further configured to determine environmental noise, and to determine a frequency of the pure tone acoustic signal based on the environmental noise determined at each of the plurality of frequencies.

16. The apparatus of claim 1, wherein the processor is further configured to adjust a volume of the pure tone acoustic signal in dependence upon a measurement of the energy in the sampled signal.

17. A computer-implemented method for tracking motion of a target, the method comprising:
transmitting a pure tone acoustic signal;
sampling a signal reflected by a target ensonified by the transmitted pure tone acoustic signal; and
estimating motion of the target based on analysis of a plurality of Discrete Fourier Transformations (DFTs) of the sampled signal, wherein the plurality of DFTs are represented by a plurality of energy values in each of a respective plurality of frequency bins, such that the analysis is based on a time-variance of energy values in at least a pair of frequency bins centered around the frequency of the transmitted pure tone acoustic signal, and any DFT of the plurality of DFTs is configured such that either:
a boundary between two adjacent frequency bins is at the frequency of the transmitted pure tone acoustic signal; or
the center of a frequency bin is at the frequency of the transmitted pure tone acoustic signal; and
outputting the estimated motion of the target.

18. The method of claim 17, wherein:
the method is performed on a sleep-tracking apparatus;
the sleep-tracking apparatus comprises a means for performing sleep analysis based on the estimated motion of the target; and
the output includes an alarm within a predetermined time of the means for performing sleep analysis determining arousal or light sleep of the target.

19. The method of claim 18, further comprising: determining environmental noise, and to determine a frequency of the pure tone acoustic signal based on the environmental noise determined at each of the plurality of frequencies.

20. A computer program product being tangibly embodied on a non-transitory computer-readable storage medium and including instructions which, when executed by a processor, is arranged to perform the instructions comprising:
transmitting a pure tone acoustic signal;
sampling a signal reflected by a target ensonified by the transmitted pure tone acoustic signal; and
estimating motion of the target based on analysis of a plurality of Discrete Fourier Transformations (DFTs) of the sampled signal, wherein the plurality of DFTs are represented by a plurality of energy values in each of a respective plurality of frequency bins, such that the analysis is based on a time-variance of energy values in at least a pair of frequency bins centered around the frequency of the transmitted pure tone acoustic signal, and any DFT of the plurality of DFTs is configured such that either:
a boundary between two adjacent frequency bins is at the frequency of the transmitted pure tone acoustic signal; or
the center of a frequency bin is at the frequency of the transmitted pure tone acoustic signal; and
outputting the estimated motion of the target.

\* \* \* \* \*